US008206400B2

(12) United States Patent
Falahee

(10) Patent No.: US 8,206,400 B2
(45) Date of Patent: *Jun. 26, 2012

(54) PERCUTANEOUS TRANSLAMINAR FACET FIXATION SYSTEM

(75) Inventor: Mark H. Falahee, Ann Arbor, MI (US)

(73) Assignee: US Spine, Inc., Salt Lake City, UT (US)

( * ) Notice: Subject to any disclaimer, the term of this patent is extended or adjusted under 35 U.S.C. 154(b) by 1636 days.

This patent is subject to a terminal disclaimer.

(21) Appl. No.: 11/484,521

(22) Filed: Jul. 11, 2006

(65) Prior Publication Data

US 2006/0264953 A1 Nov. 23, 2006

Related U.S. Application Data

(63) Continuation-in-part of application No. 10/683,076, filed on Oct. 10, 2003, now Pat. No. 7,608,094.

(60) Provisional application No. 60/417,543, filed on Oct. 10, 2002.

(51) Int. Cl.
*A61B 17/60* (2006.01)
*A61B 17/70* (2006.01)
*A61B 17/88* (2006.01)
*A61F 2/00* (2006.01)

(52) U.S. Cl. .................. 606/104; 606/247; 606/279

(58) Field of Classification Search ............. 606/86 R, 606/99, 104, 116, 117, 205, 220; 81/347, 81/352; 269/3, 6, 95
See application file for complete search history.

(56) References Cited

U.S. PATENT DOCUMENTS

| | | | |
|---|---|---|---|
| 1,412,961 A * | 4/1922 | Periolat | 81/3.7 |
| 5,423,858 A * | 6/1995 | Bolanos et al. | 606/220 |
| 5,527,312 A | 6/1996 | Ray | |
| 5,558,674 A | 9/1996 | Heggeness et al. | |
| 6,257,565 B1 * | 7/2001 | Houston et al. | 269/249 |
| 6,485,518 B1 | 11/2002 | Cornwall et al. | |
| 6,540,747 B1 | 4/2003 | Marino | |
| 6,648,893 B2 | 11/2003 | Dudasik | |
| 6,706,048 B2 * | 3/2004 | Hermann et al. | 606/139 |
| 6,811,567 B2 | 11/2004 | Reiley | |
| 6,949,123 B2 | 9/2005 | Reiley | |
| 6,966,930 B2 | 11/2005 | Arnin et al. | |
| 7,041,136 B2 | 5/2006 | Goble et al. | |
| 7,060,068 B2 | 6/2006 | Tromanhauser et al. | |
| 2004/0111093 A1 | 6/2004 | Chappuis | |
| 2004/0225360 A1 | 11/2004 | Malone | |
| 2004/0254575 A1 | 12/2004 | Obenchain et al. | |
| 2005/0124993 A1 | 6/2005 | Chappuis | |
| 2005/0149030 A1 | 7/2005 | Serhan et al. | |
| 2005/0273110 A1 | 12/2005 | Boehm, Jr. et al. | |
| 2006/0004367 A1 | 1/2006 | Alamin et al. | |
| 2006/0111779 A1 | 5/2006 | Petersen | |
| 2006/0111780 A1 | 5/2006 | Petersen | |

* cited by examiner

*Primary Examiner* — Anu Ramana
(74) *Attorney, Agent, or Firm* — Phillips Ryther Winchester, LLC; Matthew D. Thayne

(57) ABSTRACT

A percutaneous facet fixation system minimally invasive, reproducible, efficient, and effective. Capable of immediate stabilization of a facet joint complex, the instrumentation and methods may be used with C-arm and/or endoscopic visualization.

21 Claims, 2 Drawing Sheets

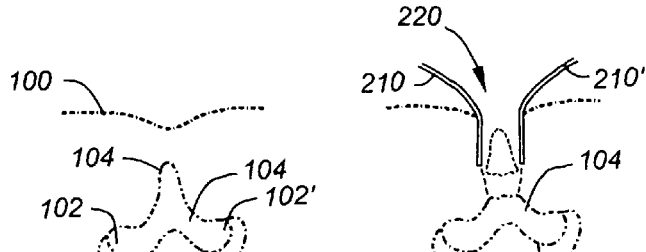
Fig - 1
Fig - 2
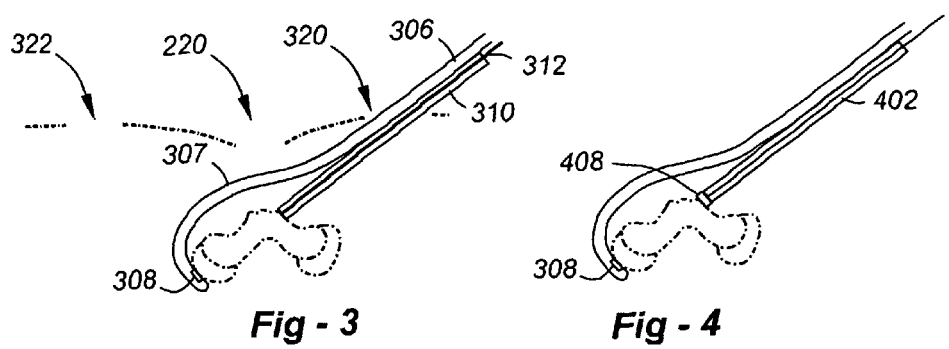
Fig - 3
Fig - 4
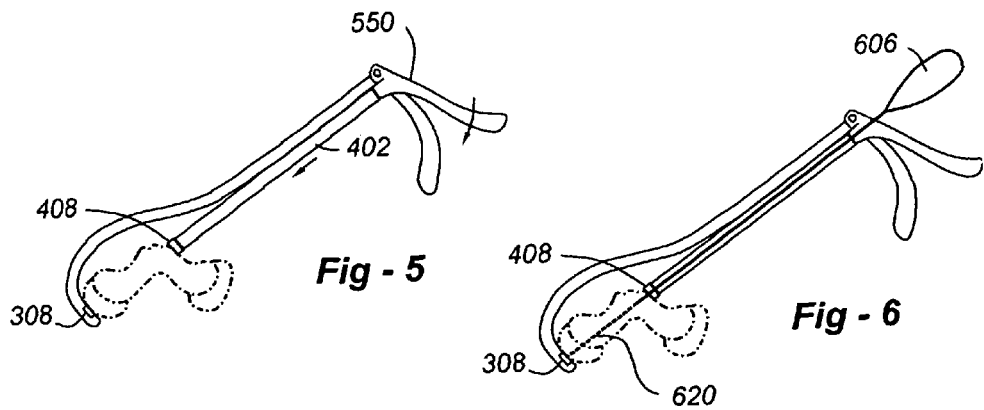
Fig - 5
Fig - 6

PERCUTANEOUS TRANSLAMINAR FACET FIXATION SYSTEM

REFERENCE TO RELATED APPLICATION

This application is a continuation-in-part of co-pending U.S. patent application Ser. No. 10/683,076, filed Oct. 10, 2003, which claims priority from U.S. Provisional Patent Application Ser. No. 60/417,543, filed Oct. 10, 2002, the entire content of each of which is incorporated herein by reference.

FIELD OF THE INVENTION

This invention relates generally to spine surgery and, in particular, to a percutaneous or minimally invasive facet fixation system.

BACKGROUND OF THE INVENTION

For patients with a high degree of spinal instability (e.g. fractures), or in revision surgery, a combination anterior/posterior fusion is indicated at one or more levels. Fusing both the front and back provides a high degree of stability for the spine and a large surface area for the bone fusion to occur. The disc may be approached either as an anterior lumbar interbody fusion (ALIF), or as a posterior lumbar interbody fusion (PLIF). Transforaminal lumbar interbody fusion (TLIF) fuses the anterior and posterior columns of the spine through a single posterior approach. All such procedures are well known to those of skill in the art.

To further stabilize vertebral segments, posterior instrumentation is often performed in conjunction with an interbody fusion. The most commonly used posterior instrumentation system in use today is pedicle screw fixation. The major disadvantage to this technique is the necessity of major muscle dissection, which can lead to morbidity and scarring. Another disadvantage is the bulkiness of the pedicle/rod system, which has the potential of being prominent, palpable, or painful.

Facet screw fixation offers the advantage of placing a single screw across each articulating facet joint to immobilize a motion segment, thereby reducing the amount of hardware (and therefore exposure) necessary. Existing techniques, however, still demand relatively open procedures, such that the need remains for a facet fixation system compatible with minimally invasive surgical (MIS) procedures.

SUMMARY OF THE INVENTION

The present invention is a percutaneous system of facet fixation that is minimally invasive, reproducible, efficient, and effective. Capable of immediate stabilization of a facet joint complex, the instrumentation and methods may be used with C-arm and/or endoscopic visualization. The apparatus and methods are primarily used to augment interbody fixation (ALIF, TLIF, PLIF) in patients with degenerative disc disease or spinal instability resulting from arthritic changes.

BRIEF DESCRIPTION OF THE DRAWINGS

FIG. 1 is a highly-simplified drawing that shows the facet joints of a patient to which this invention is applicable;

FIG. 2 is a drawing showing a midline posterior approach to the spine using retractors and removal of the spinous process to the junction of the lamina;

FIG. 3 is a drawing that shows a guide wire passed by C-arm or endoscopic guidance to a facet joint in conjunction with the lower arm of the facet gun passed through a separate incision;

FIG. 4 is a drawing that shows the upper arm of the facet gun, including a locking nut, inserted along the track of the guide wire of FIG. 3;

FIG. 5 shows the handle of a facet gun compressed;

FIG. 6 shows how a bolt is driven through the superficial and deep nuts, thereby fusing the facet joint;

DETAILED DESCRIPTION OF THE INVENTION

Figure 7:
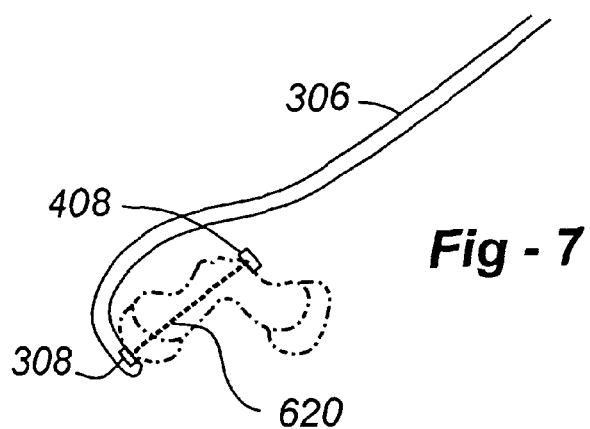
FIG. 7 shows the fused joint with the lower arm of the facet gun still in position.

Reference is now made to the drawings, wherein FIG. 1 is a highly-simplified drawing that shows the facet joints 102, 102' of a patient 100 to which this invention is applicable. The proximal spinous process is indicated at 104. The lamina is indicated at 106.

The patient is placed in a prone position under general anesthetic. A C-arm is preferably utilized to determine fixation level and approach for incision. A 1.0-inch incision (or thereabouts) 220 is made in midline over the proximal spinous process 104. (For L4-L5 fixation, the incision made over L4 spinous process.) As shown in FIG. 2, the spinous process removed to junction of lamina, allowing access angle to facet joints bilaterally.

FIG. 3 is a drawing that shows the way in which a guide wire 312 is passed by C-arm or endoscopic guidance to a facet joint in conjunction with a facet gun including arm 306 according to the invention. This approach is achieved via a separate lateral incision 320. The lower arm of facet gun contains a deep locking nut 308 abutting lateral surface of the superior articular process comprising the facet joint. The deep locking nut is positioned in alignment with the guide wire 312 by C-arm past the facet joint. Arm 306 preferably includes an outwardly bent portion 307 to clear and remaining bony protrusions.

FIG. 4 is a drawing that shows the upper arm of the facet gun 402, and a superficial locking nut 408, also inserted along the track of the guide wire of FIG. 3. Through appropriate modification, a fastener may be used without the need for locking nut 408. The locking nut 408 is inserted over the guide sleeve of lower arm, making contact with the laminar surface on the opposing side of the spine. As shown in FIG. 5, the handle of the facet gun compressed, holding the nuts 408, 308 onto upper and under surface of facet joint.

Figure 12:
FIG. 12 is a drawing of a bolt including a drill bit tab useful to the invention.

Referring to FIG. 6, a previously selected facet bolt, preferably with drill bit head 998 as shown in FIG. 12, is inserted into barrel of upper facet gun sleeve. The bolt is driven through superficial and deep nuts using a manually operated tool 606, passing through facet joint, locking into the superficial nut and compressing the joint together.

Figure 8:
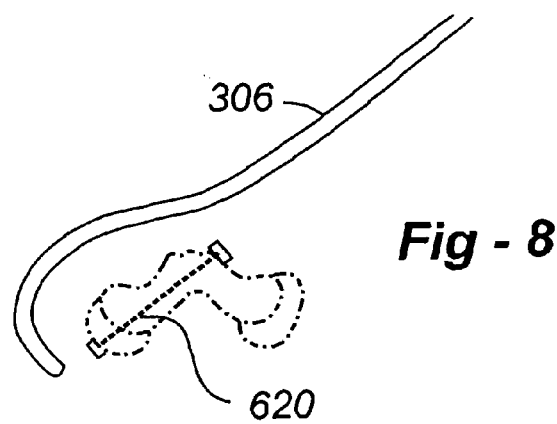
FIG. 8 shows the removal of the lower arm.

The upper arm of facet gun is removed in FIG. 7. The lower arm is pushed deeper, disengaging itself from the deep nut, and the arm and guide wire are removed as shown in FIG. 8. The procedure is then repeated for the opposite side using a separate lateral incision 322.

Figure 9:
FIG. 9 shows an alternative embodiment of a nut applicable to the invention, including fixation spikes.
Figure 10:
FIG. 10 shows the use of a washer according to the invention, which may be wedge-shaped and which may use fixation spikes.
Figure 11:
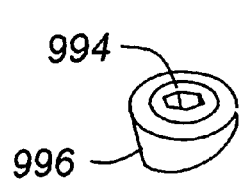
FIG. 11 is a drawing that shows the way in which a bolt head seats inside of a top nut through a click lock.

FIG. 9 is a drawing that shows an alternative nut useful in conjunction with the invention, including an optional wedge-shape and, independent of that, the use of fixation spikes 990 operative to dig into the bone, particularly during and after compression of the joint. FIG. 10 shows how the upper nut, in particular, may be replaced with a washer 992 devoid of threats. Optionally, as with the lower locking nut, the shape of the washer in FIG. 10 may be wedge-shaped or contoured to match the facet surface, and may include optional fixation spikes as well. FIG. 11 shows the way in which a bolt head 994 may seat inside of the top nut 996, and locking in position with click stops (not visible in the picture).

I claim:

1. A system for percutaneously fusing a facet joint using a translaminar approach, comprising:
    a first fastener portion;
    a lower arm adapted to hold the first fastener portion behind a superior articular process of a facet joint,
    an upper arm including a distal tip adapted to access an opposing outer surface of a lamina;
    a second fastener portion operatively connected with the upper arm; and
    a threaded fastener configured to be separately coupled to the first and second fastener portions so as to fuse the joint through compression.

2. The system of claim 1, wherein the first and second fastener portions are deep and superficial nuts, respectively.

3. The system of claim 1, wherein the fastener comprises a threaded bolt.

4. The system of claim 3, wherein the threaded bolt comprises a drill bit head.

5. The system of claim 1, wherein the fastener is configured to be inserted into the first fastener portion.

6. The system of claim 5, wherein the fastener comprises a head that is configured to seat inside the first fastener portion.

7. The system of claim 6, wherein the head is configured to seat inside the first fastener portion and lock into position with respect to the first fastener portion by way of a click stop.

8. The system of claim 6, wherein the first fastener portion comprises a nut.

9. The system of claim 6, wherein the first fastener portion comprises a washer.

10. The system of claim 9, wherein the washer is shaped to conform with a surface of the superior articular process.

11. The system of claim 10, wherein the washer is at least generally wedge shaped.

12. The system of claim 9, wherein the washer comprises a plurality of fixation spikes.

13. A method of percutaneously fusing a facet joint using a translaminar approach, comprising the steps of:
    holding a first fastener portion behind a superior articular process of a facet joint; and
    passing a second fastener portion across a lamina to the first fastener portion, thereby fusing the joint through compression.

14. The method of claim 13, wherein the first fastener portion comprises a nut.

15. The method of claim 13, wherein the first fastener portion comprises a washer.

16. The method of claim 13, wherein the second fastener portion comprises a bolt configured to engage the first fastener portion.

17. The method of claim 16, wherein the second fastener portion further comprises a nut or a washer.

18. The method of claim 17, wherein at least one of the first and second fastener portions comprises a plurality of fixation spikes.

19. A system for percutaneously fusing a facet joint using a translaminar approach, comprising:
    a first fastener portion;
    a lower arm adapted to hold the first fastener portion behind a superior articular process of a facet joint,
    an upper arm including a distal tip adapted to access an opposing outer surface of a lamina;
    a second fastener portion operatively connected with the upper arm; and
    a fastener comprising a bolt, wherein the fastener is configured to be inserted into the first fastener portion, wherein the fastener is configured to connect the first and second fastener portions so as to fuse the joint through compression, and wherein the fastener comprises a head that is configured to seat inside the first fastener portion and, once seated, lock into place within the first fastener portion.

20. The system of claim 19, wherein the first fastener portion comprises a washer, and wherein the second fastener portion comprises a washer.

21. The system of claim 19, wherein the first fastener portion comprises a nut, and wherein the second fastener portion comprises a nut.

* * * * *